(12) United States Patent
Van Bentem

(10) Patent No.: US 6,510,345 B1
(45) Date of Patent: Jan. 21, 2003

(54) SYSTEM AND METHOD OF BRIDGING A TRANSRECEIVER COIL OF AN IMPLANTABLE MEDICAL DEVICE DURING NON-COMMUNICATION PERIODS

(75) Inventor: Maarten M. P. E. Van Bentem, Dieren (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/556,454

(22) Filed: Apr. 24, 2000

(51) Int. Cl.$^7$ .................................................. A61N 1/08
(52) U.S. Cl. ........................................ 607/60; 607/32
(58) Field of Search ............................. 607/60, 30, 31, 607/32; 128/903, 901

(56) References Cited

U.S. PATENT DOCUMENTS

| | | | | |
|---|---|---|---|---|
| 4,494,545 A | * | 1/1985 | Slocum et al. | 128/903 |
| 4,681,111 A | * | 7/1987 | Silvian | 128/903 |
| 5,697,958 A | * | 12/1997 | Paul et al. | 128/901 |
| 5,817,130 A | * | 10/1998 | Cox et al. | 128/901 |
| 6,301,504 B1 | * | 10/2001 | Silvian | 607/60 |

* cited by examiner

*Primary Examiner*—Kennedy Schaetzle
(74) *Attorney, Agent, or Firm*—Thomas F. Woods; Eric R. Waldkoette; Tom G. Berry

(57) ABSTRACT

The present invention discloses a method of and a system for preventing unwanted alternating current magnetic fields transmitted from an external source from disrupting electrical circuitry within an implantable medical device, while permitting desired communications between the implantable medical device and a programmer detected in proximity to the implantable medical device. The implantable medical device is capable of communication with at least one implantable lead position within a heart of a patient. The method includes activating an electrical device to create a short circuit in parallel with an inductive transreceiver coil of the implantable medical device, thereby shorting out the inductor transreceiver coil. In this mode, alternating current magnetic fields do not effect electrical circuitry within the implantable medical device. The method further includes detecting a direct current magnetic field indicating the presence of a programmer located in proximity to the implantable medical device. The electrical device shorting out the inductive transreceiver coil is deactivated and thereby opened during detection of the presence of the programmer in proximity to the implantable medical device such that the implantable medical device and the programmer can communicate via the inductive transreceiver coil.

58 Claims, 13 Drawing Sheets

SYSTEM AND METHOD OF BRIDGING A TRANSRECEIVER COIL OF AN IMPLANTABLE MEDICAL DEVICE DURING NON-COMMUNICATION PERIODS

THE FIELD OF THE INVENTION

The present invention relates generally to a system and method used in conjunction with an implantable medical device. More specifically, the present invention relates to a system and method of bridging a transreceiver coil of an implantable medical device during non-communication periods, thereby blocking unwanted magnetic induction signals transmitted from external sources in the absence of a programmer located proximal to the implantable medical device.

BACKGROUND OF THE INVENTION

Implantable medical device systems known in the art comprise several components, including an implantable medical device, such as a pacemaker or a defibrillator, pacing and/or sensing leads, and a programmer. The leads connect the implantable medical device to the heart of a patient. An implantable medical device, such as a pacemaker or a defibrillator, commonly stores a variety of different types of diagnostic data which assist a clinician or a physician (operator) in evaluating both the operation of the heart of the patient and the operation of the implanted medical device. The specific diagnostic data stored by the implantable medical device includes a variety of information, including a real-time event recording of pacing events.

The programmer of the implantable medical device system is a microprocessor-based device which is a stand-alone unit commonly located at a hospital or within a physician's office. The operator positions the programmer proximal the implantable medical device. The programmer is capable of communicating with the implantable medical device and displaying information on a display screen. Depending upon the specific programmer, the programmer may be capable of reading information from and transmitting information to the implantable medical device. Other programmers are only capable of monitoring or receiving information from an implantable medical device, without the capability of transmitting information to the implantable medical device. The programmer of the implantable medical device system provides multiple functions, including assessing lead performance during a pacemaker or a defibrillator implantation, receiving feedback information from the implantable medical device for use by the operator, and, depending upon the specific programmer, programming the implantable medical device.

An analyzer, which is sometimes a sub-component of the programmer and sometimes an individual component, is also a microprocessor-based device. The analyzer assists the operators in assessing the electrical performance of a pacing lead system used in conjunction with an implantable medical device system. The analyzer utilizes the programmer as a control and display platform.

There are numerous instances in which diagnostic data must be monitored during an adjustment procedure or must be retrieved from the implantable medical device and displayed on the display screen of the programmer. For example, during a routine follow-up visit of the patient to a clinic, it is often necessary to retrieve information related to the implantable medical device or the patient. Second, during a visit to a clinic, a physician may want to perform a series of tests on the patient and view a variety of information related to the implantable medical device and the patient. Third, during a medical procedure on the patient unrelated to the implantable medical device, it may be necessary to monitor and/or adjust various parameters of the implantable medical device prior to the medical procedure to ensure adequate performance of the implantable medical device during the unrelated medical procedure.

Implantable medical devices and programmers communicate with each other by means of an inductive transreceiver coil located within the programmer and an inductive transreceiver coil located within the implantable medical device. In addition, the implantable medical device includes a programmer detection system which detects the presence of a programmer in proximity to the implantable medical device. For example, the programmer detection system is in a first state when a programmer is not proximal to the implantable medical device. However, when a programmer is located proximal to the implantable medical device, the programmer detection system changes from the first state to a second state. With the programmer detection system in the second state, indicating the presence of a programmer proximal to the implantable medical device, a communication system within the implantable medical device is permitted to communicate with the programmer via the inductive transreceiver coils as previously discussed.

The patents listed in Table 1 are examples of different systems and methods utilizing a transreceiver coil within an implantable medical device.

| U.S. Pat. No. | Inventor | Issue Date |
| --- | --- | --- |
| 4,340,038 | Brian D. McKean | Jul. 20, 1982 |
| 5,741,315 | Chik Yam Lee et al. | Apr. 21, 1998 |
| 5,796,254 | Everett R. Andrus | Aug. 18, 1998 |
| 5,944,023 | Theodore A. Johnson et al. | Aug. 31, 1999 |
| 5,951,594 | Harry B. A. Kerver | Sep. 14, 1999 |
| 6,009,878 | Koen J. Weijand et al. | Jan. 04, 2000 |

All patents listed in Table 1 above are hereby incorporated by reference herein in their respective entireties. As those or ordinary skill in the art will appreciate readily upon reading the Summary of the Invention, Detailed Description of the Preferred Embodiments, and claims set forth below, many of the devices and methods disclosed in the patents of Table 1 may be modified advantageously by using the teachings of the present invention.

One disadvantage of prior art implantable medical devices relates to external alternating current (AC) magnetic fields radiating from various sources, such as anti-theft systems used within businesses, shops, or libraries used to prevent goods from being removed from the business without properly paying for or checking out the goods. These anti-theft systems produce dynamic AC magnetic fields between two sources, such as two gates located on either side of an exit path. In many retail businesses or shops, items for purchase include a magnetic device secured to the item. The magnetic device is removed once the item has been purchased. If the magnetic device is not removed prior to exiting the shop or business, the AC magnetic field between the two sources (gates) sense the presence of the magnetic device. Most often, an audio and/or visual alarm is triggered, inferring that the item was removed from the business or shop without proper payment or that the magnetic device was not properly removed at the time of purchase.

Another method of protecting goods is a tag that consists of a printed inductive coil (L) in parallel with a capacitor (C). The tag is detected by gates near the exit of shops due to the specific frequency of the magnetic field produced by the gates. The tag can be made inoperative by a large magnetic field produced by an apparatus near the paying station, which destroys the parallel L, C connection.

The AC magnetic fields transmitted between the two sources do not interact with the communication system of the implantable medical device since they do not have the proper syntax. However, these dynamic AC magnetic fields do produce an undesired load or unintentional drain on the power supply of the implantable medical device due to the external AC magnetic field acting on the inductive transreceiver coil of the implantable medical device. Depending upon the strength of the AC magnetic field and the length of time that the AC magnetic field is acting upon the inductive transreceiver coil of the implantable medical device, the implantable medical device will enter a reset state or mode. The implantable medical device will no longer pace the heart of the patient or sense parameters from the heart of the patient. This may cause the patient to go into cardiac arrest. Once the external AC magnetic field is no longer acting on the implantable medical device, the implantable medical device resumes normal operation, such as pacing and sensing.

Therefore, there is a need for a system which will prevent unwanted AC magnetic fields transmitted from external sources from disrupting electrical circuitry, including the power supply, within an implantable medical device. However, the system should permit desired communications between the implantable medical device and a programmer when the programmer is located in proximity to the implantable medical device.

SUMMARY OF THE INVENTION

The present invention overcomes the disadvantages of the prior art by providing a method of and an apparatus for communicating with a programmer located in proximity to the implantable medical device while preventing unwanted magnetic signals transmitted from other external sources from disrupting electrical circuitry within the implantable medical device.

The present invention has certain objects. That is, the present invention provides solutions to certain problems existing in the prior art such as: (a) an inability to prevent unwanted AC magnetic fields transmitted from an external source from disrupting electrical circuitry within an implantable medical device; (b) an inability to prevent unwanted AC magnetic fields detected by an inductive transreceiver coil of an implantable medical device from draining a power supply of the implantable medical device; (c) an inability for an implantable medical device to continue pacing and sensing the heart of a patient due to an unwanted AC magnetic field acting upon an inductive transreceiver coil of the implantable medical device; (d) an inability to short out an inductive transreceiver coil at all times other than when an external programmer is detected in proximity to an implantable medical device; (e) an inability to provide a short circuit in parallel with an inductive transreceiver coil when a programmer is not detected in proximity to an implantable medical device; and (f) an inability to provide an open circuit in parallel with an inductive transreceiver coil when a programmer is detected in proximity to an implantable medical device.

The system and method of the present invention provides certain advantages, including: (a) the ability to prevent unwanted AC magnetic fields transmitted from an external source from disrupting electrical circuitry within an implantable medical device; (b) the ability to prevent unwanted AC magnetic fields detected by an inductive transreceiver coil of an implantable medical device from draining a power supply of the implantable medical device; (c) the ability for an implantable medical device to continue pacing and sensing the heart of a patient by blocking unwanted AC magnetic fields acting upon an inductive transreceiver coil of the implantable medical device; (d) the ability to short out a inductive transreceiver coil at all times other than when a programmer is detected in proximity to an implantable medical device; (e) the ability to provide a short circuit in parallel with an inductive transreceiver coil when a programmer is not detected in proximity to an implantable medical device; and (f) the ability to provide an open circuit in parallel with an inductive transreceiver coil when a programmer is detected in proximity to an implantable medical device.

The system and method of the present invention has certain features, including a switching device connected in parallel with an inductive transreceiver coil of the implantable medical device. The switching device is connected to a programmer detector of the implantable medical device. If the programmer detector detects the presence of a programmer in proximity to the implantable medical device, the switching device is opened, thereby creating an open circuit (high impedance path) in parallel with the inductive transreceiver coil. The implantable medical device can communicate with the programmer via the inductive transreceiver coil. However, if the programmer detector does not detect the presence of a programmer in proximity to the implantable medical device, the switching device is closed, thereby creating a short circuit (low impedance path) in parallel with the inductive transreceiver coil.

Another feature of the present invention is that unless and until the programmer detector of the implantable medical device detects the presence of a programmer proximal to the implantable medical device, any signals received by the inductive transreceiver coil from any external source do not affect the remaining portions of the implantable medical device. More specifically, a power source of the implantable medical device is not drained due to external AC magnetic field acting upon the inductive transreceiver coil. An implantable medical device with a drained power source will no longer pace the heart of the patient or sense parameters from the heart of the patient. This may cause the patient to go into cardiac arrest.

Another feature of the present invention is the activation of an electrical device electrically coupled in parallel with the inductive transreceiver coil, thereby creating a short circuit in parallel with the inductive transreceiver coil due to the lack of detection of a programmer located in proximity to the implantable medical device. The electrical device is deactivated during detection of the presence of a programmer in proximity to the implantable medical device.

Yet another feature of the present invention is a switching device connected in parallel with the inductive transreceiver coil which blocks unwanted AC magnetic fields transmitted from an external source from interacting with a communications system within the implantable medical device in the absence of a programmer located in proximity to the implantable medical device. The switching device permits desired magnetic fields from a programmer to interact with the implantable medical device when the programmer is located in proximity to the implantable medical device, thereby permitting communication between implantable medical device and the programmer.

Other objects, advantages, and features of the invention will become apparent by referring to the appended drawings, detailed description, and claims.

Description OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
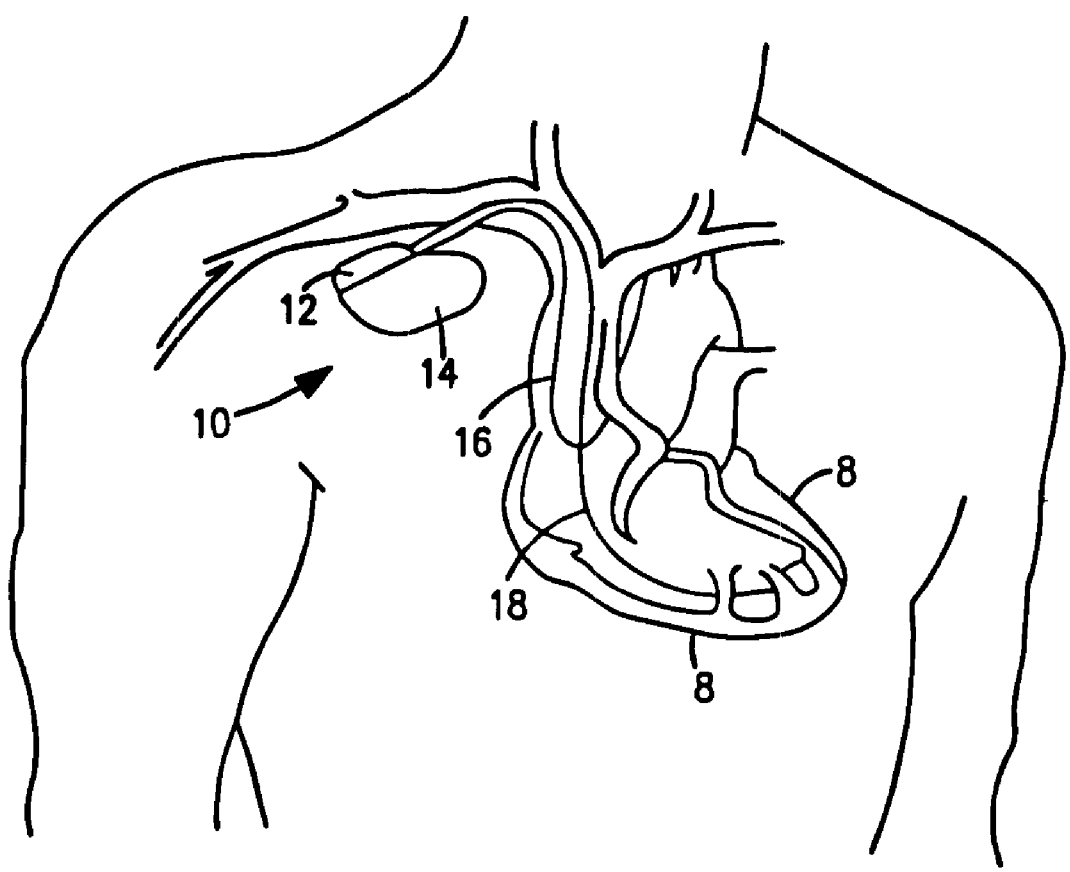
FIG. 1 is a simplified schematic view of one embodiment of an implantable medical device.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
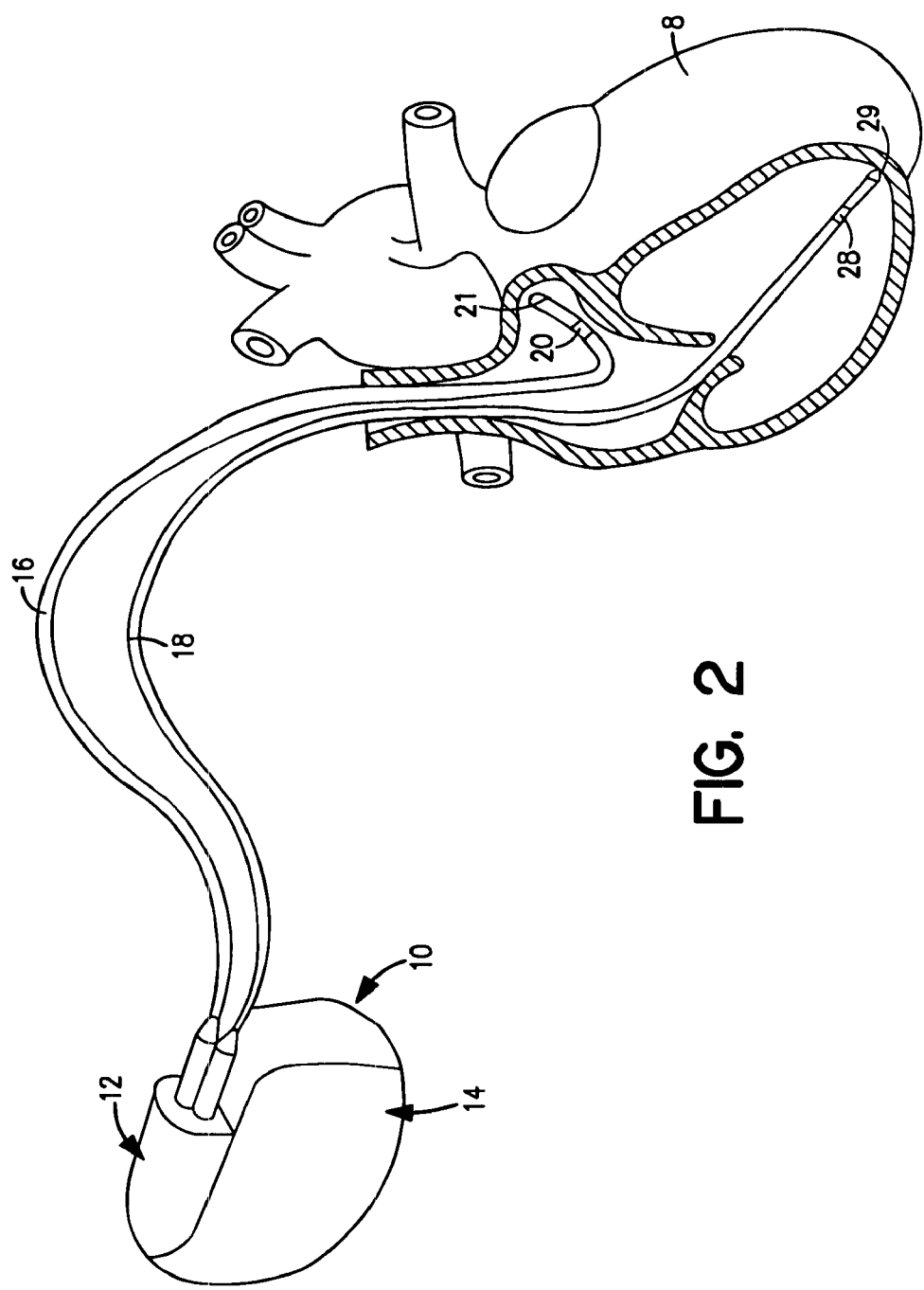
FIG. 2 is a simplified illustration of an implantable medical device with leads positioned within passageways of a heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
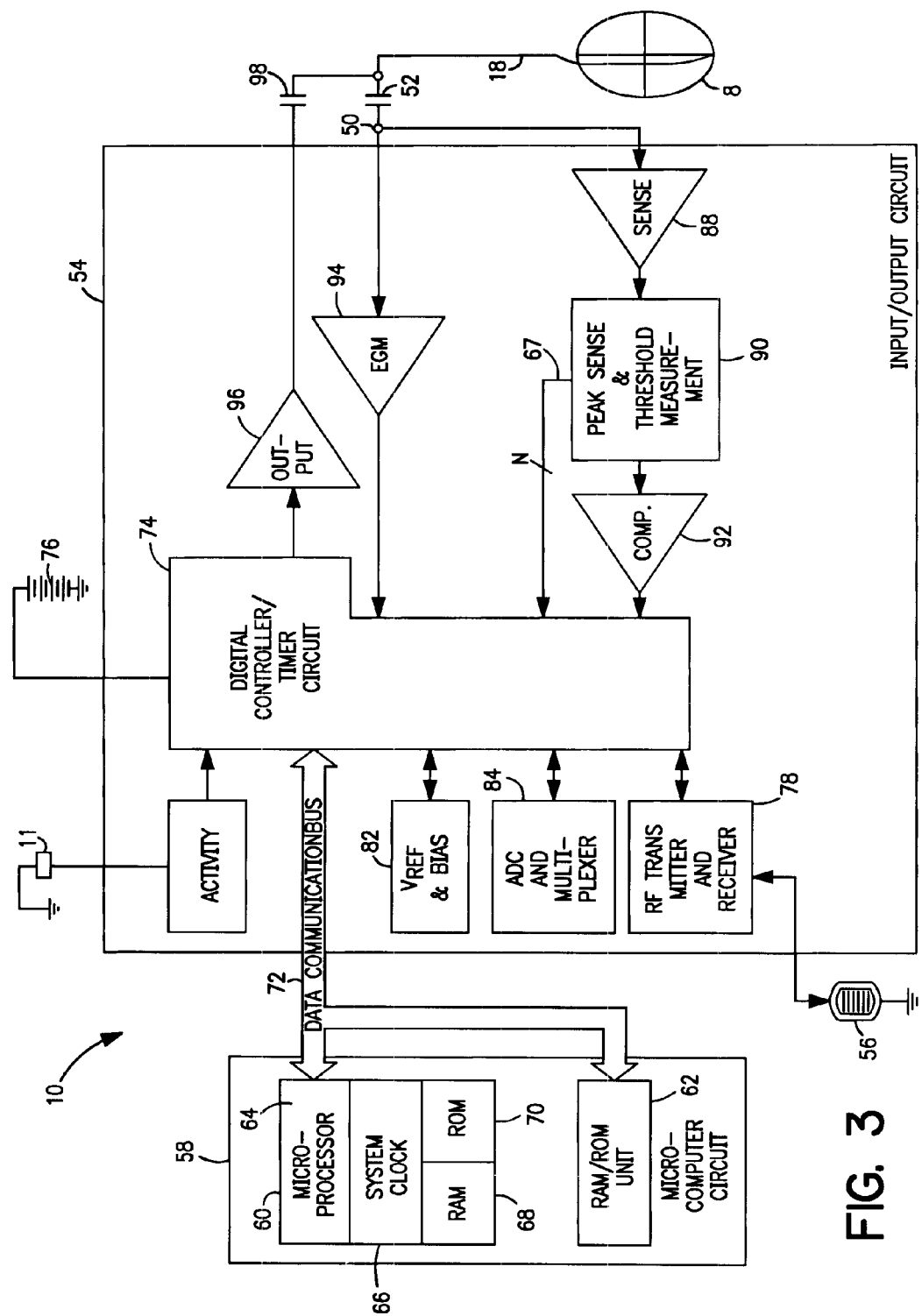
FIG. 3 is a block diagram illustrating the constituent components of an implantable medical device.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

Figure 6:
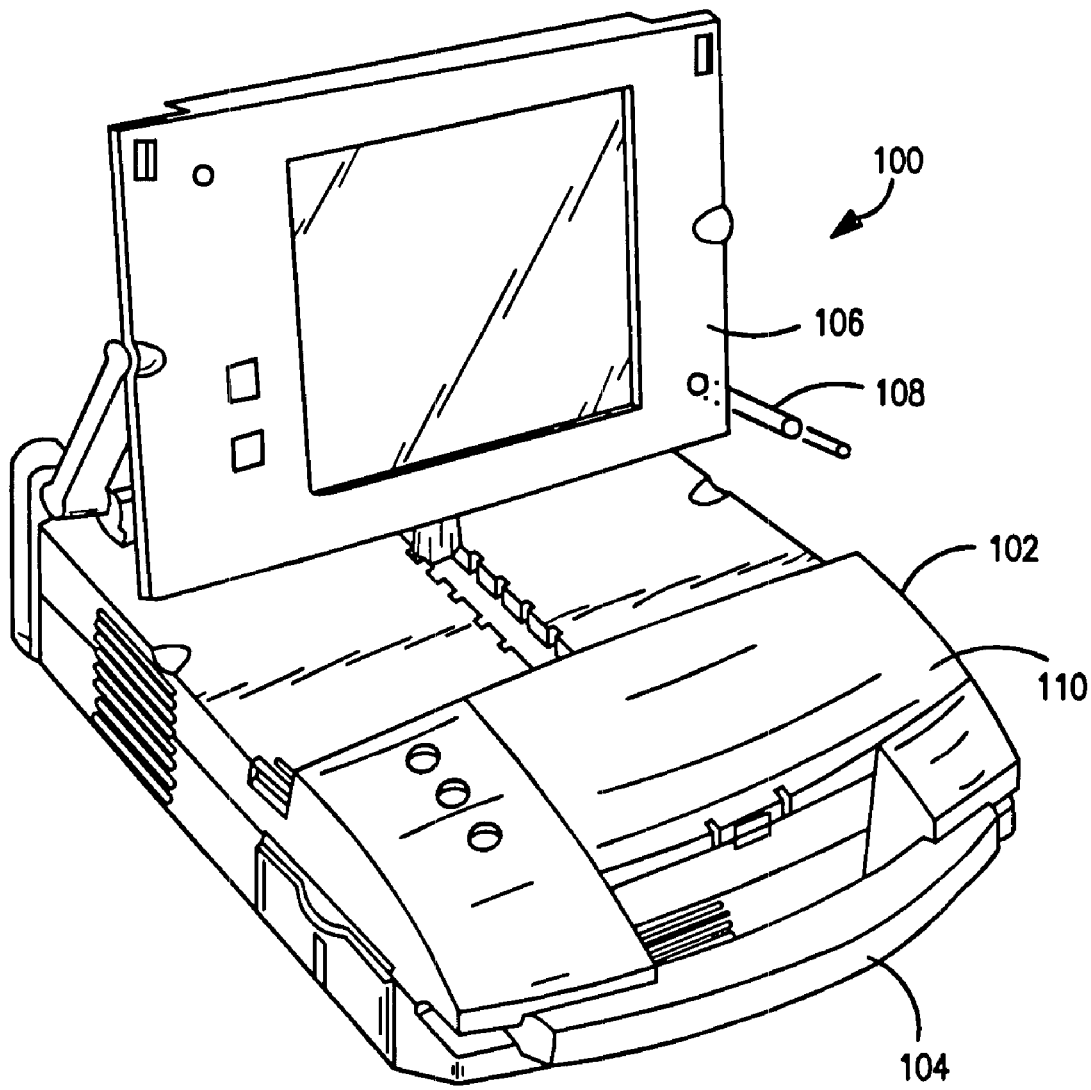
FIG. 6 is a perspective view of a programmer unit used in conjunction with an implantable medical device.

IMD 10 in FIG. 3 is most preferably programmable by means of an external programming unit (shown in FIG. 6). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
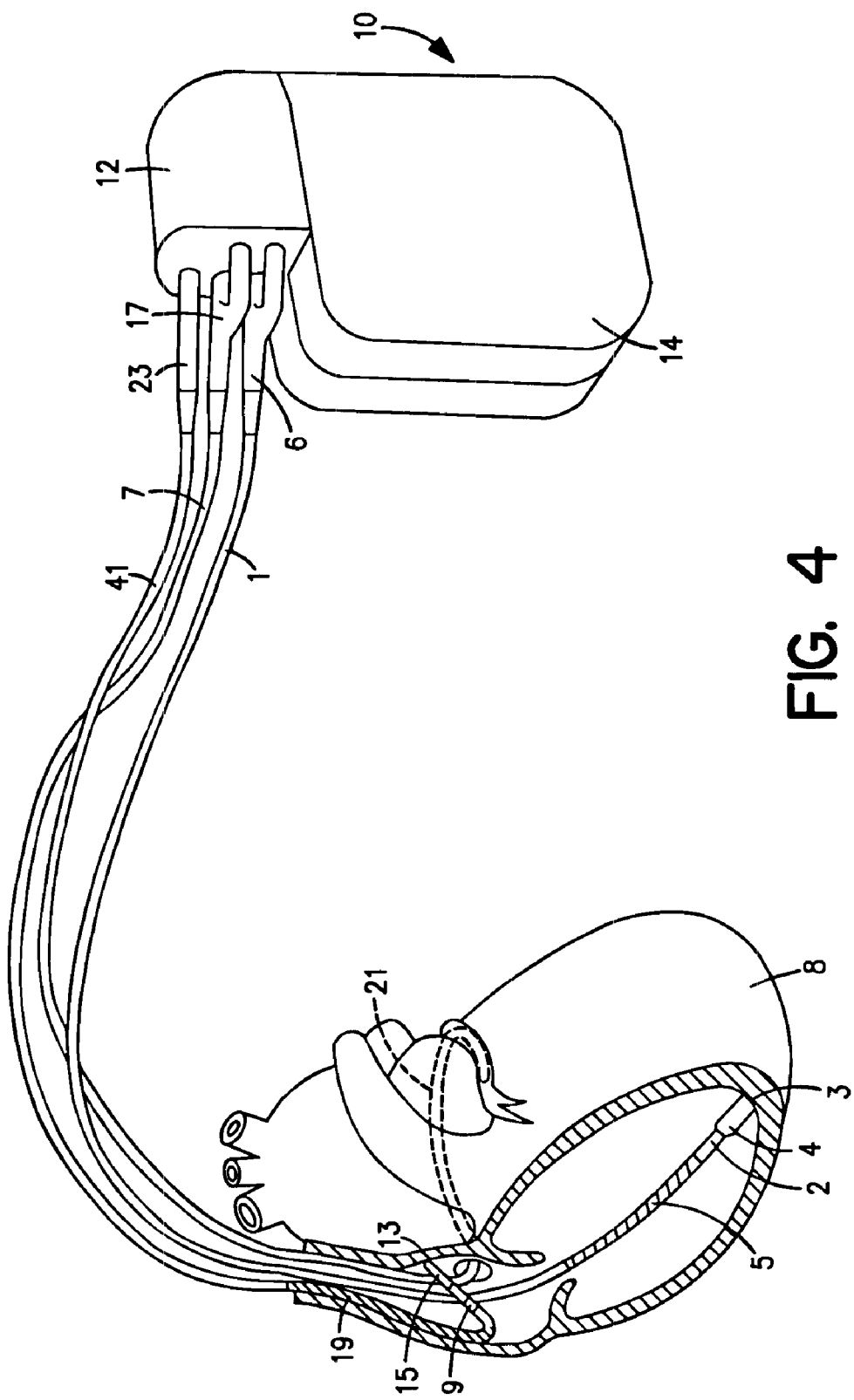
FIG. 4 is a simplified schematic view of an implantable medical device with leads positioned within passageways of a heart.
Figure 5:
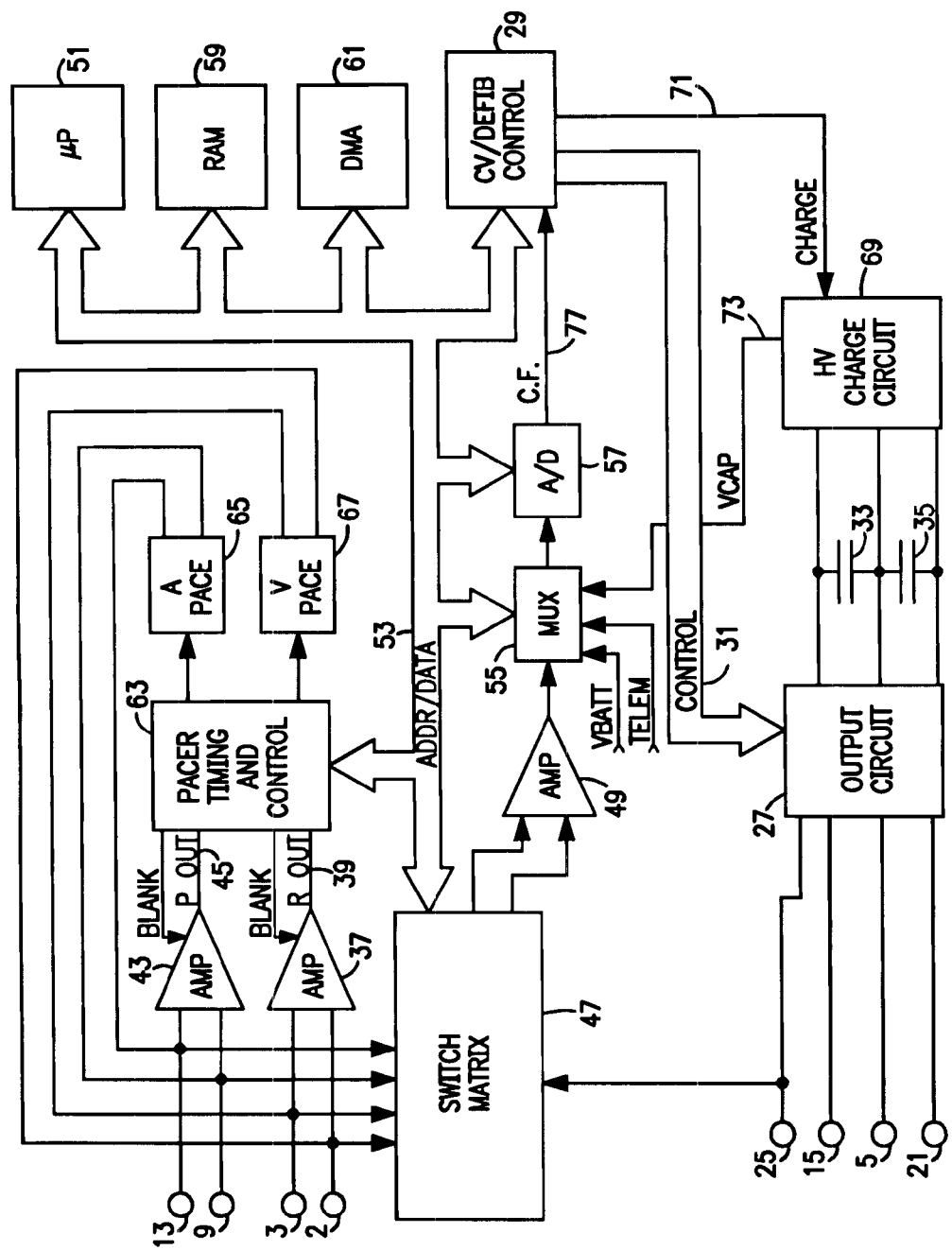
FIG. 5 is a partial block diagram illustrating one embodiment of an implantable medical device.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

FIG. 6 is a perspective view of programmer 100, which illustrates one embodiment of a programmer that may be used in conjunction with the present invention. It is understood by those in the art that other programmers known in the art may be substituted for programmer 100 without deviating from the present invention. Programmer 100 includes various features, such as outer housing 102, carrying handle 104, articulate display screen 106, stylus 108, and analyzer 110.

Display screen 106 is disposed on the upper surface of housing 102. Display screen 106 folds down in a close position when programmer 100 is not in use, thereby reducing the size of programmer 100 and protecting the display surface of display screen 106 during transportation and storage. Display screen 106 is operatively coupled to computer circuitry disposed within housing 102 and is adapted to provide a visual display of graphics and/or numerical and alphanumeric data under control of the computer circuitry.

Display screen 106 is provided with touch-sensitivity capability, such that a user can interact with the internal computer by touching the display area of display screen 106 with stylus 108. It is believed that those of ordinary skill in the computer art will be familiar with touch-sensitivity display technology, and the details of implementation of such display will not be described further herein. Display screen 106 is the primary input medium for programmer 100 and therefore preferably has sufficient resolution to support operations including selection, gestures, annotation, and character recognition.

Analyzer 110, which can be a separate unit capable of connection to programmer 100 via connecting cables, provides a medium for an operator to run a series of diagnostic tests during an implantation procedure of an IMD, such as IMD 10 previous discussed. For example, a continuous-time wave form or single complex wave form can be analyzed by analyzer 110 and displayed on display screen 106 from a variety of implanted leads, such as a lead position in an atrium or ventricle of heart 8 (shown in FIGS. 1, 2, and 4).

Figure 7:
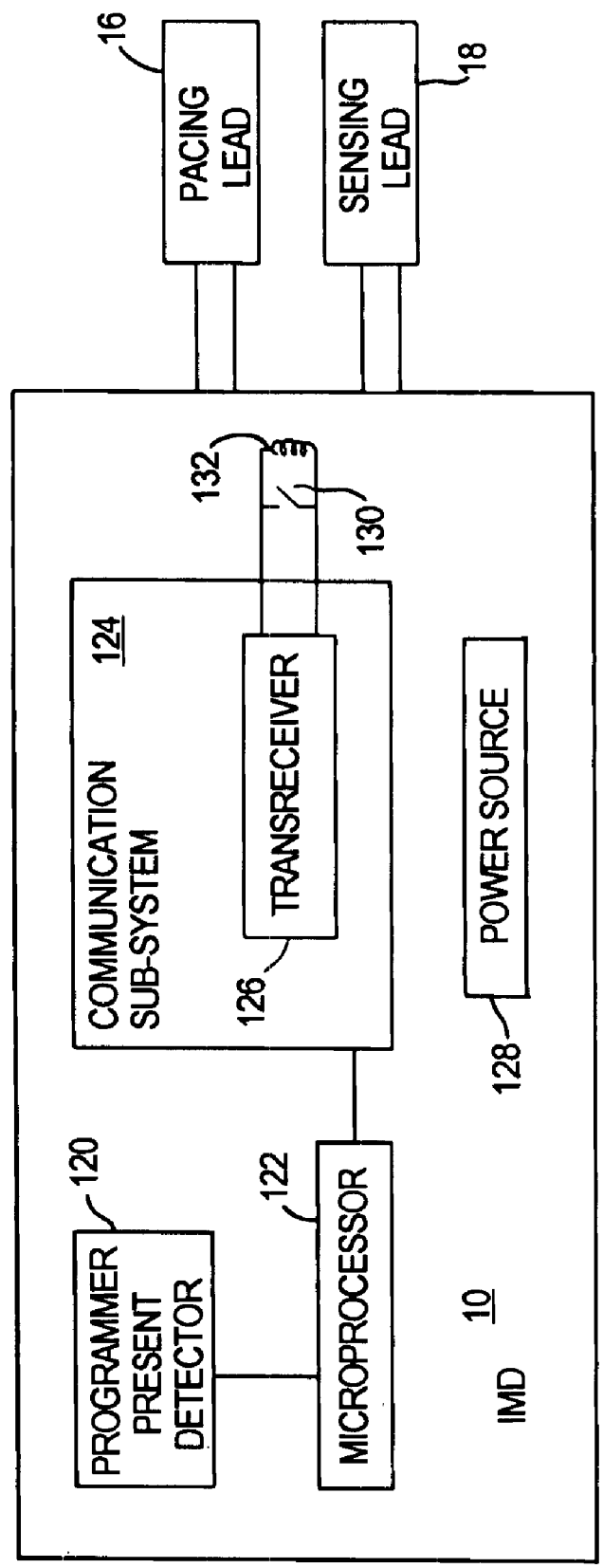
FIG. 7 is a simplified block diagram illustrating an implantable medical device in accordance with the present invention.

FIG. 7 is a simplified block diagram illustrating IMD 10 in accordance with the present invention. It is understood by those in the art that IMD 10 includes various components and elements not shown in FIG. 7. In particular, numerous elements described with reference to FIGS. 3 and 5 are not shown in FIG. 7 for clarity purposes. IMD 10 shown in FIG. 7 includes programmer present detector 120, microprocessor 122, communication sub-system 124 having transreceiver 126, power source 128, switch 130, and inductive transreceiver coil 132.

Sensing lead 18 senses electrical signals attendant to the depolarization and re-polarization of heart 8 (shown in FIGS. 1, 2, and 4). Pacing lead 16 provides pacing pulses, which cause de-polarization of cardiac tissue in the vicinity of the distal ends of pacing lead 16. While pacing and sensing leads 16 and 18 are shown each as a single lead, it is understood that pacing and sensing leads 16 and 18 may have unipolar or bipolar electrodes disposed thereon, as is well known in the art.

Programmer present detector 120 detects the presence of a programmer, such as programmer 100 shown in FIG. 6, in proximity to IMD 10. In one preferred embodiment, programmer present detector 120 includes either a Hall sensor, Reedswitch, or polling transreceiver. The Hall sensor, Reedswitch, or polling transreceiver of programmer present detector 120 is capable of detecting a direct current (DC) magnetic field radiating from a magnet of a programmer in proximity to IMD 10. As is known by those in the art and will be further described with reference to FIG. 8, programmers include a power source which includes a magnet. This magnet radiates DC magnetic fields which can be detected by programmer present detector 120.

Communication sub-system 124 communicates with a programmer located in proximity to IMD 10 via inductive transreceiver coil 132. Communication sub-system 124 may include various designs without deviating from the present invention. For example, communication sub-system may include hardware components that provide information in the form of bit streams to and from a programmer. Alternatively, communication sub-system 124 may include a software program that can compose and interpret transmitted and received information bits. Transreceiver 126 is the sub-component of communication sub-system 124 which transmits information as information in the form of bit streams to a programmer via inductive transreceiver coil 132 and receives data signals or information bit streams from a programmer via inductive transreceiver coil 132. In one preferred embodiment, inductive transreceiver coil 132 facilitates transmission of inductive signals and/or magnetically coupled signals between IMD 10 and a programmer.

While it is not shown for clarity purposes, power source 128 is electrically coupled to programmer present detector 120, microprocessor 122, and communication sub-system 124. Power source 128 provides the power necessary to operate the components of IMD 10. Microprocessor 122 is shown electrically coupled to programmer present detector 120 and communication sub-system 124. However, in one preferred embodiment, microprocessor 122 is not electrically coupled to programmer present detector 122. Microprocessor may incorporate microcomputer circuit 58 shown and discussed with reference to FIG. 3 and/or microprocessor 51 shown and discussed with reference to FIG. 5.

Switch 130 represents an electrical device positioned in parallel with inductive transreceiver coil 132. Switch 130 is capable of providing either an open circuit or a short circuit in parallel with inductive transreceiver coil 132. More specifically, if programmer present detector 120 detects the presence of a programmer in proximity to IMD 10, switch 130 is opened, thereby providing an open circuit, high impedance path in parallel with inductive transreceiver coil 132. In this configuration, information in the form of bit streams transmitted from an inductive coil of the programmer can be received by inductive transreceiver coil 132 and forwarded to communication sub-system 124 via transreceiver 126. Conversely, if programmer present detector does not detect the presence of a programmer in proximity to IMD 10, switch 130 is closed, thereby providing a short circuit, low impedance in parallel with inductive transreceiver coil 132. In this configuration, unwanted noise signals, such as alternating current (AC) magnetic fields radiating from an external magnetic source, will not interact with any components of IMD 10. Prior art IMDs do not include switch 130. Therefore, unwanted noise signals affect various components of prior art IMDs. In particular, power source 128 of IMD 10 may be drained due to the unwanted AC magnetic fields affecting transceiver coil 132. A drained power source will inhibit IMD 10 from properly pacing heart 8 or sensing signals from heart 8.

As previously discussed programmer present detector 120 detects the presence of a programmer in proximity to IMD 10. For example, programmer present detector 120 is in a first state when a programmer is not proximal to IMD 10. With programmer present detector 120 in the first state, inductive transreceiver coil 132 is isolated from the rest of IMD 10 by a parallel short circuit formed by switch 130. Thus, any external signals received by inductive transreceiver coil 132 are not transmitted to and do not affect other components of IMD 10. However, when a programmer is located proximal to IMD 10, programmer present detector 120 changes from the first state to a second state. With programmer present detector 120 in the second state, indicating the presence of a programmer proximal to IMD 10, communication sub-system 124 is permitted to communicate with the programmer via inductive transreceiver coil 132, since switch 130 provides an open circuit in parallel with inductive transreceiver coil 132.

Prior art IMDs do not include switch 130 connected in parallel with inductive transreceiver coil 132. External AC magnetic fields radiating from various sources, such as anti-theft systems used within businesses, shops, or libraries, have an overall negative impact upon prior art IMDs. Anti-theft systems produce dynamic AC magnetic fields between two sources, such as two gates located on either side of an exit path. In many retail businesses or shops, items for purchase include a magnetic device secured to the item. The magnetic device is removed once the item has been purchased. If the magnetic device is not removed prior to exiting the shop or business, the AC magnetic field between the two sources (gates) senses the presence of the magnetic device. Most often, an audio and/or visual alarm is triggered.

Another method of protecting goods is a tag that consists of a printed inductive coil (L) in parallel with a capacitor (C). The tag is detected by gates near the exit of shops due to the specific frequency of the magnetic field produced by the gates. The tag can be made inoperative by a large magnetic field produced by an apparatus near the paying station, which destroys the parallel L, C connection.

The AC magnetic fields transmitted between the two sources do not interact with communication sub-system 124 of IMD 10 when a patient is located between the two sources since these fields do not have the proper syntax. However, these dynamic AC magnetic fields do produce a drain on power source 128 due to the external AC magnetic field acting on inductor transreceiver coil 132. Depending upon the strength of the AC magnetic fields and the length of time that the AC magnetic fields are acting upon inductive transreceiver coil 132 (the time the patient is located within the magnetic field between the two sources), prior art IMDs will go into a reset state or mode. Prior art IMDs no longer pace heart 8 or sense parameters from heart 8. This may cause the patient to go into cardiac arrest. Once the external AC magnetic fields are no longer acting on prior art IMDs, prior art IMDs resume normal operation, such as pacing and sensing.

With the present invention, external AC magnetic fields do not affect power source 128, or any other sub-components of IMD 10. Rather, switch 130, when in a closed state, provides a short circuit in parallel with inductor transreceiver coil 132. Therefore, the unwanted AC magnetic fields received by inductive transreceiver coil 132 are isolated on inductor transreceiver coil 132 and do not affect any sub-component of IMD 10, including power source 128.

Figure 8:
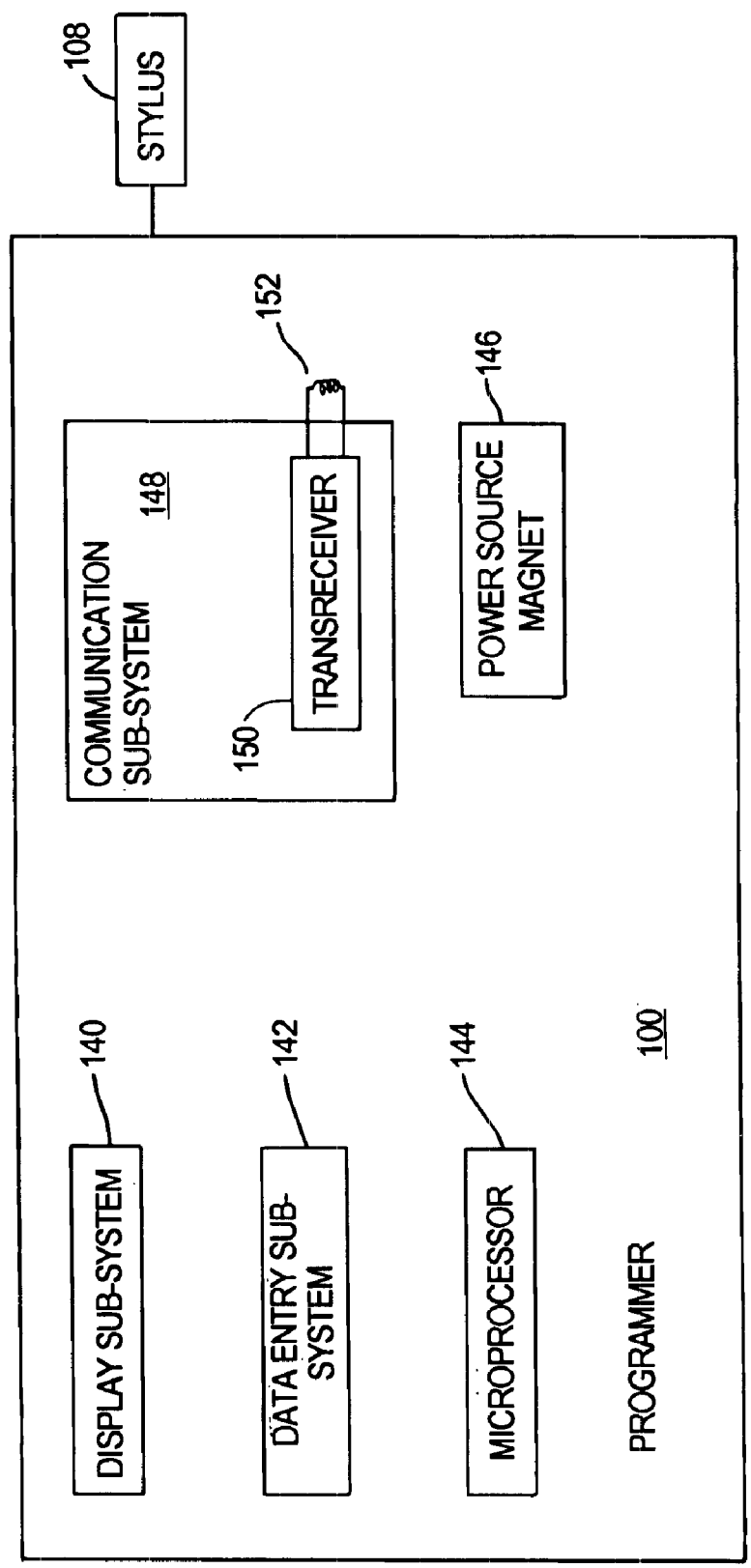
FIG. 8 is a simplified block diagram illustrating one embodiment of a programmer.

FIG. 8 is a simplified block diagram illustrating one embodiment of programmer 100 corresponding to the present invention. Programmer 100 includes display sub-system 140, data entry sub-system 142, microprocessor 144, power source magnet 146, communication sub-system 148 having transreceiver 150, inductive transreceiver coil 152, and stylus 108. For clarity purposes, the electrical coupling between the various sub-systems and the power source, which includes power source magnet 146, are not shown. Likewise, the electrical coupling between microprocessor 144 and various sub-systems are not shown for clarity purposes. However, it is understood by those in the art that each of the sub-systems shown in FIG. 8 are electrically coupled to the outer sub-components. However, these couplings have also been illuminated for clarity purposes. Display sub-system 140 corresponds with display screen 106, shown in FIG. 6, while data entry sub-system 142 corresponds to both a keypad of programmer 100 and the touch-sensitive attributes of display screen 106. Stylus 108 provides a link between an operator of programmer 100 and display sub-system 140 and data entry sub-system 142.

Power source magnet 146 is a portion of the power source of programmer 100. As is understood by those in the art, power source magnet 146 radiates a DC magnetic field. It is this DC magnetic field which programmer present detector 120 of IMD 10, shown in FIG. 7, is attempting to detect and recognize. Communication sub-system 148 interacts with communication sub-system 124 of IMD 10 via transreceivers 126 and 150, and inductive transreceiver coils 132 and 152.

When programmer 100 is located in proximity to IMD 10, programmer 100 communicates with IMD 10 via communication sub-systems 124 and 148. In one preferred embodiment, the communication is a one-way communication. For example, programmer 100 may receive and monitor information from IMD 10. In another preferred embodiment, there may be a two-way communication between IMD 10 and programmer 100. More specifically, communication sub-system 124 of IMD 10 may be capable of sending, while communication sub-system 148 of programmer 100 may be capable of receiving, information or data relating to parameters of IMD 10 and relating to parameters of heart 8. Also, communication sub-system 148 of programmer 100 may be capable of sending, and communication sub-system 124 of IMD 10 may be capable of receiving, programmable information capable of programming or altering characteristics of IMD 10. Due to various signals received from IMD 10, it may be necessary to alter the parameters of IMD 10 to optimize pacing and sensing of heart 8.

Figure 9A:
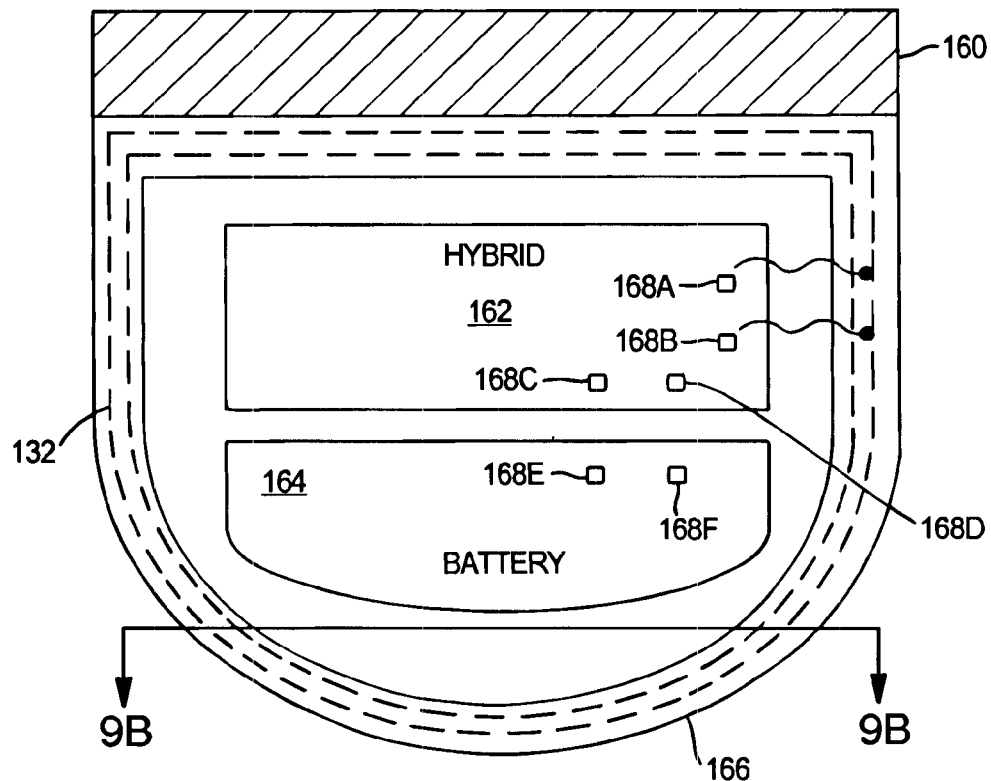
FIG. 9A is a schematic view of one embodiment of an implantable medical device in conjunction with the present invention.
Figure 9B:
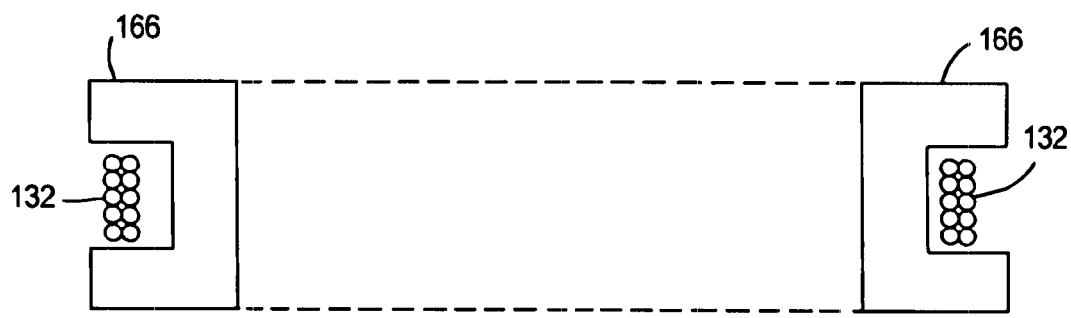
FIG. 9B is a cross-sectional view of the implantable medical device shown in FIG. 9A as seen from lines 9B—9B.

FIG. 9A is a schematic view of one embodiment IMD without an exterior casing 10 in conjunction with the present invention. FIG. 9B is a cross-sectional view of IMD 10 shown in FIG. 9A as seen from lines 9B—9B. FIGS. 9A and 9B illustrate one embodiment of the interconnection of inductor transreceiver coil 132 in parallel with switch 130 to other sub-components of IMD 10. IMD 10 includes head exterior 160, hybrid 162, battery 164, mechanical frame 166, and bond pads 168A–168F. As shown in FIGS. 9A and 9B, inductor transreceiver coil 132 is positioned within the framework of mechanical frame 166, surrounding both hybrid 162 and battery 164.

In one preferred embodiment, inductive transreceiver coil 132 is an aircoil wrapped within mechanical frame 166 and kept together by an adhesive, such as glue. Inductive transreceiver coil 132 is in electrical connection with hybrid 162 via bond pads 168A and 168B. Likewise, hybrid 162 is in electrical connection with battery 164 via bond pads 168C–168F. Hybrid 162 includes all internal components of IMD 10 previously described with reference to FIGS. 3, 5, and 7 other than a power source, which is represented by battery 164. In one preferred embodiment, hybrid 162 is a printed circuit board interconnecting several components including programmer present detector 120, microprocessor 122, communication sub-system 124, transreceiver 126, and switch 130. In the embodiment shown in FIGS. 9A and 9B, switch 130, shown in FIG. 7, is interconnected between bond pads 168A and 168B immediately within hybrid 162 such that switch 130 provides a short circuit or an open circuit in parallel with inductive transreceiver coil 132.

Thus, switch 130 isolates inductive transreceiver coil 132 or provides an electrical path between inductive transreceiver coil 132 and circuitry within hybrid 162.

Figure 10:
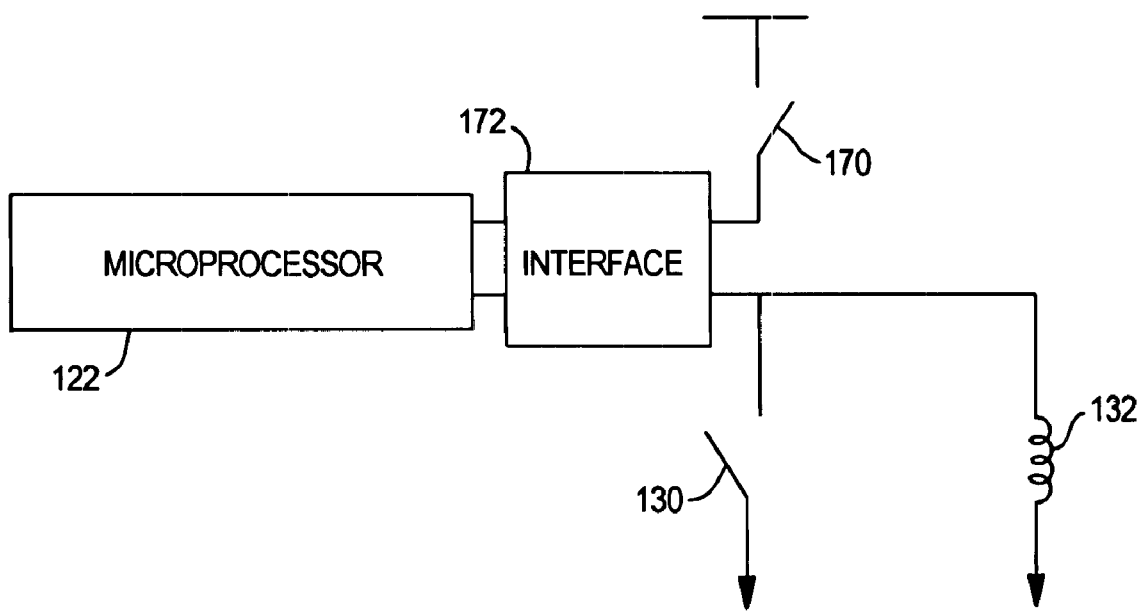
FIG. 10 is an electrical diagram illustrating portions of an implantable medical device in accordance with the present invention.

FIG. 10 is an electrical diagram illustrating portions IMD 10 in accordance with the present invention. IMD 10 includes microprocessor 122, switch 130, inductor transreceiver coil 132, switch 170, and interface 172. Switch 170 represents a portion of programmer present detector 120 shown in FIG. 7. Under normal circumstances, programmer present detector 120 is attempting to detect the presence of programmer 100 in proximity to IMD 10. Programmer present detector is attempting to detect the presence of a large DC magnetic field radiating from power source magnet 146 of programmer 100. In the embodiment shown in FIG. 10, switch 170 remains open until the detection of programmer 100. Once a DC magnetic field of programmer 100 acts on switch 170, switch 170 automatically closes due to the DC magnetic field.

With switch 170 open, a signal is transmitted to microprocessor 122 via interface 172 indicating the status of switch 170. Microprocessor 122 then prompts interface 172 via a second signal to maintain switch 130 in a closed position. With switch 130 in a closed position, a short circuit is provided in parallel with inductive transreceiver coil 132. Thus, any unwanted AC magnetic fields radiating from various external sources, such as those previously discussed, will not affect other sub-systems or components of IMD 10, specifically power source 128. However, once programmer present detector 120 detects the presence of programmer 100 in proximity to IMD 10, switch 170 is closed. A closing of switch 170 provides a signal to microprocessor 122 via interface 172 indicating the status of switch 170. Microprocessor 122 then prompts interface 172 to transmit a second signal to switch 130 to open. Therefore, switch 130 provides an open circuit in parallel with inductive transreceiver coil 132. At this point, communication signals can be transmitted between communication sub-system 124 of IMD 10 and communication sub-system 148 of programmer 100. In one preferred embodiment, switch 170 represents a Hall sensor or a Reedswitch. In another preferred embodiment, switch 130 represents either a metal oxide semiconductor device, a bipolar junction transistor, a junction field effect transistor (JFET) a thyristor, a triac, or a Reedswitch.

Figure 11:
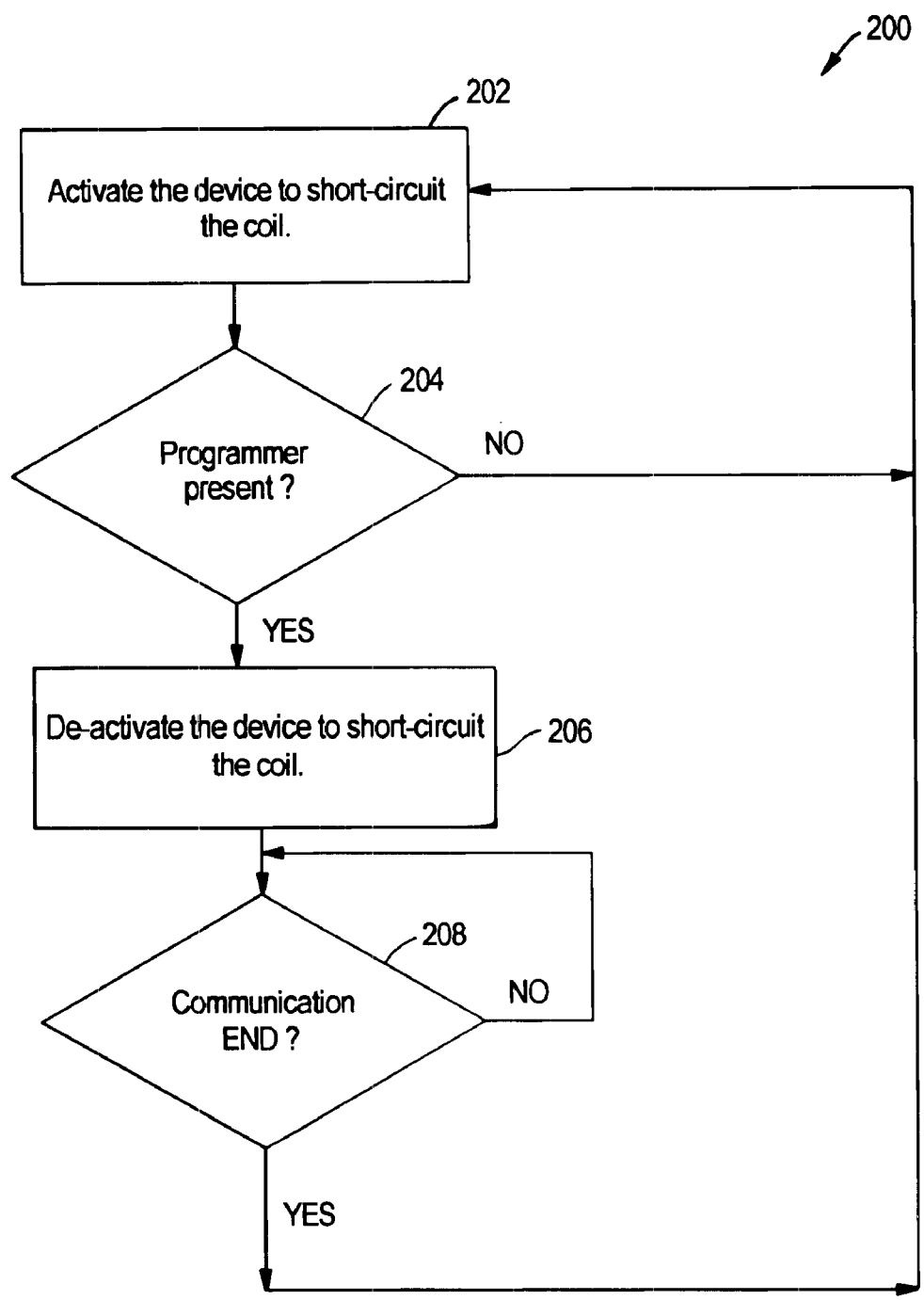
FIG. 11 is a simplified flow chart describing a method of present invention.

FIG. 11 illustrates simplified flow chart 200 describing a method of the present invention. At step 202, the device to short circuit inductor transreceiver coil 132 is activated. More specifically, a signal is sent to switch 130 which closes switch 130, thereby providing a short circuit in parallel with inductive transreceiver coil 132. In one preferred embodiment, the step of activating the device to short circuit inductor transreceiver coil 132 includes providing a first current to the device from microprocessor 122 such that the device acts as a short circuit.

At decision step 204, it is determined if programmer 100 is located in proximity to IMD 10. Programmer present detector 120 detects the presence of a DC magnetic field which indicates the presence of programmer 100 in proximity to IMD 10. If programmer 100 is not detected in proximity to IMD 10, the device which short circuits inductor transreceiver coil 132 continues to be activated (Step 202). If programmer 100 is detected in proximity to IMD 10, the device which short circuits inductive transreceiver coil is deactivated (Step 206). More specifically, a second signal is sent to switch 130 in parallel with inductive transreceiver coil 132 such that switch 130 is open, thereby creating an open circuit, rather than a short circuit. With switch 130 acting as an open circuit, communication between IMD 10 and programmer 100 is permitted via inductive transreceiver coil 132.

At decision step 208, it is determined whether the communication between IMD 10 and programmer 100 is complete. Specifically, programmer present detector 120 determines whether programmer 100 is still in proximity to IMD 10. If programmer 100 is still in proximity to IMD 10, it is assumed that the communication between IMD 10 and programmer 100 is not complete. Conversely, if programmer 100 is no longer in proximity to IMD 10, switch 130 is activated to create a short circuit in parallel with inductive transreceiver coil 132 (Step 202).

Figure 12A:
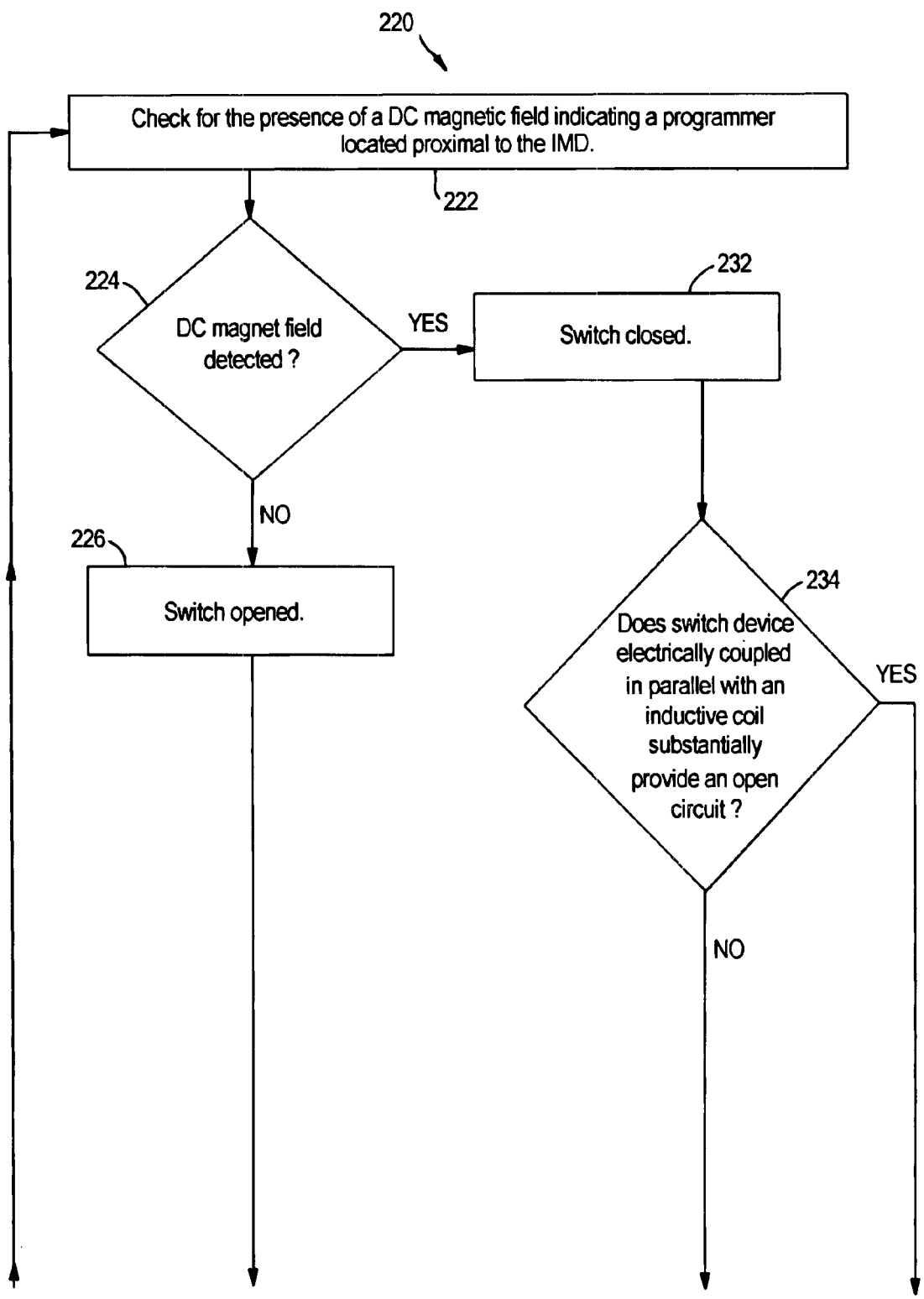
FIG. 12 is a detailed flow chart illustrating a method of the present invention.
Figure 12B:
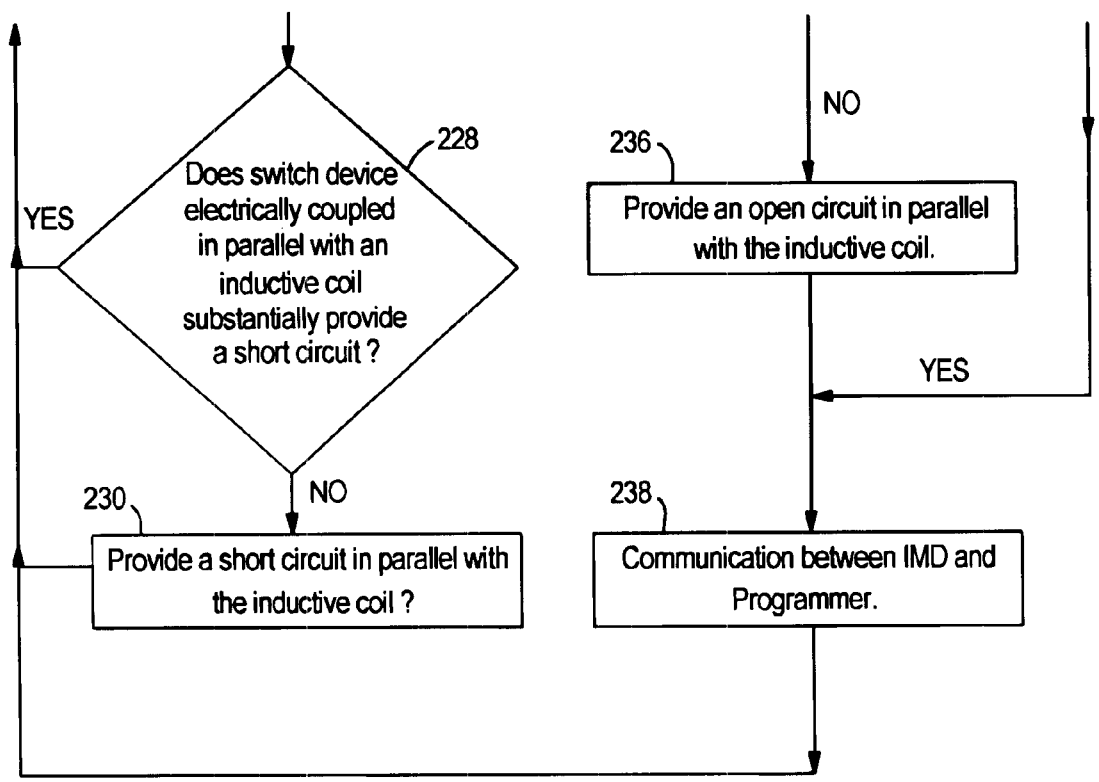

FIG. 12 illustrates detailed flow chart 220 describing a method of the present invention. At step 222, the presence of a DC magnetic field indicating that programmer 100 is located proximal to IMD 10 is checked. At decision step 224, it is determined if a DC magnetic field is detected by programmer present detector 120. If a DC magnetic field is not detected, switch 170 associated with programmer present detector 120 is automatically opened and remains in an open position (step 226). At decision step 228, with switch 170 opened, it is determined whether switch 130 electrically coupled in parallel with inductive transreceiver coil 132 substantially provides a short circuit. If switch 130 does provide a short circuit, step 222 is repeated. If switch 130 does not provide a short circuit, a signal is sent to switch 130 via interface 172 to provide a short circuit in parallel with inductor transreceiver coil 132 (step 230). At this point, the programmer 100 is not located in proximity to IMD 10. Therefore, the short circuit of switch 130 prevents any unwanted AC magnetic fields transmitted from external sources acting upon inductor transreceiver coil 132 from affecting other components or devices of IMD 10. Specifically, power source 120 will not be drained due to AC magnetic fields acting upon inductor transreceiver coil 132.

At step 232, once a DC magnetic field is detected, switch 170 is closed and remains in a closed position due to the DC magnetic field of programmer 100. At decision step 234, it is determined whether switch 130 in parallel with inductor transreceiver coil 132 provides an open circuit. At step 236, if switch 130 does not provide an open circuit, a signal is sent to switch 130 from microprocessor 122 via interface 172 to provide an open circuit. At step 238, once an open circuit is provided by switch 130, communication between IMD 10 and programmer 100 may begin. In one preferred embodiment, the path for communication between IMD 10 and programmer 100 will remain open via inductive transreceiver coil 132 as long as programmer present detector 120 of IMD 10 detects the presence of programmer 100 in proximity to IMD 10. In another preferred embodiment, the functionality of programmer present detector 120 as defined by switch 170 may be overridden by a software protocol which indicates that programmer 100 is present as long as IMD 10 receives a communication, such as a downlink, within a preset time frame.

The preceding specific embodiments are illustrative of the practice of the invention. It is understood to be, therefore, that other expedients known to those skilled in the art or disclosed herein, may be employed without departing from the invention or the scope of the appended claims. For example, the present invention is not limited to a single switch element for either switch 130 or switch 170. Rather, there are individual elements or any combination of elements which may be used in place of switches 130 and 170. The present invention is also not limited to pacemakers or cardio defibrillators per se, but may find further applications with other implantable medical devices which have a corresponding programmer. The present invention further includes within its scope methods of making and using the implantable medical device described herein.

In the claims, means-plus-function clauses are intended to cover the structure described herein as performing the recited function and not only structural equivalents, but also equivalent structures. Thus, although a nail and a screw may not be structural equivalents in that a nail employs a cylindrical surface to secure wooden parts together, whereas a screw employs a helical surface in the environment of fastening wood parts, a nail and a screw are equivalent structures.

All printed publications, patent applications and patents referenced hereinabove are incorporated by reference herein, each in its respective entirety.

What is claimed is:

1. A method of preventing unwanted alternating current (AC) magnetic fields transmitted from an external source from disrupting electrical circuitry within an implantable medical device, while permitting desired communications between the implantable device and a programmer, the method comprising:

activating an electrical device within the implantable medical device electrically coupled in parallel with an inductive transceiver coil, thereby providing a short circuit in parallel with the inductive transreceiver coil during non-detection of the programmer in proximity to the implantable medical device by activating an electrical device within the implantable medical device electrically coupled in parallel with an inductive transceiver coil;

deactivating the electrical device during detection of the presence of the programmer in proximity to the implantable medical device, thereby providing an open circuit in parallel with the inductive transreceiver coil by activating an electrical device within the implantable medical device electrically coupled in parallel with an inductive transceiver coil; and communicating between the implantable medical device and the proximally located programmer.

2. The method of claim 1, wherein activating the electrical device further comprises:

closing a switch electrically coupled in parallel with the inductive transreceiver coil, thereby shorting out the inductive transreceiver coil.

3. The method of claim 1, wherein activating the electrical device further comprises:

providing current to a metal oxide semiconductor device such that a low impedance path is created in parallel with the inductive transreceiver coil.

4. The method of claim 1, wherein activating the electrical device further comprises:

providing current to a bipolar junction transistor such that a low impedance path is provided in parallel with the inductive transreceiver coil.

5. The method of claim 1, wherein activating the electrical device further comprises:

providing current to a junction field effect transistor such that a low impedance path is provided in parallel with the inductive transreceiver coil.

6. The method of claim 1, wherein activating the electrical device further comprises:

providing current to a thyristor such that a low impedance path is provided in parallel with the inductive transreceiver coil.

7. The method of claim 1, wherein activating the electrical device further comprises:

providing current to a triac such that a low impedance path is provided in parallel with the inductive transreceiver coil.

8. The method of claim 1, wherein activating the electrical device further comprises:

providing current to a Reedswitch such that a low impedance path is provided in parallel with the inductive transreceiver coil.

9. The method of claim 1, wherein activating the electrical device further comprises:

providing an electrical signal from a programmer detector of the implantable medical device to the electrical device indicating a lack of presence of the programmer proximal to the implantable medical device.

10. The method of claim 1, wherein deactivating the electrical device further comprises:

providing an electrical signal from a program detector of the implantable medical device to the electrical device indicating the presence of a programmer in proximity to the implantable medical device.

11. The method of claim 1, wherein deactivating the electrical device further comprises:

deactivating the electrical device during detection of the presence of a direct current magnetic field radiating from the programmer.

12. The method of claim 1, wherein communicating between the implantable medical device and the programmer further comprises:

transmitting information stored within the implantable medical device to the programmer via the inductive transreceiver coil.

13. The method of claim 1, wherein communicating between the implantable medical device and the programmer further comprises:

transmitting information to the implantable medical device from the programmer via the inductive transreceiver coil.

14. The method of claim 1, further comprising providing the implantable medical device with at least one implanatable medical electrical lead, the lead being suitable for positioning within a heart of a patient, the medical device being capable of communication with the at least one implantable lead.

15. A method of providing a communication path between an implantable medical device located within a patient and a programmer located in proximity to the implantable medical device, the implantable medical device capable of interacting with at least on e implantable lead positioned within a heart of a patient, the method comprising:

detecting a programmer located in proximity to the implantable medical device;

deactivating a low impedance device connected in parallel with an inductive transreceiver coil to electrical circuitry of the implantable medical device, the low impedance device deactivated in response to the detection of a proximally located programmer; and wherein the inductive transreceiver coil facilitates communication between the implantable medical device and the programmer.

16. The method of claim 15, wherein detecting the programmer located in proximity to the implantable medical device further comprises:

detecting a direct current magnetic field radiating from the programmer in proximity to the implantable medical device.

17. The method of claim 15, wherein deactivating the low impedance device further comprises:

opening a switch connected in parallel with the inductive transreceiver coil, thereby creating an open circuit.

18. The method of claim 15, wherein deactivating the low impedance device further comprises:

providing current to a metal oxide semiconductor device such that the metal oxide semiconductor device acts as an open circuit in parallel with the inductive transreceiver coil.

19. The method of claim 15, wherein deactivating the low impedance device further comprises:

providing current to a bipolar junction transistor such that the bipolar junction transistor acts as an open circuit in parallel with an inductor transreceiver coil.

20. The method of claim 15, wherein deactivating the low impedance device further comprises:

providing current to a junction field effect transistor such that the junction field effect transistor acts as an open circuit in parallel with an inductor transreceiver coil.

21. The method of claim 15, wherein deactivating the low impedance device further comprises:

providing current to a thyristor such that the thyristor acts as an open circuit in parallel with an inductor transreceiver coil.

22. The method of claim 15, wherein deactivating the low impedance device further comprises:

providing current to a triac such that the triac acts as an open circuit in parallel with an inductor transreceiver coil.

23. The method of claim 15, wherein deactivating the low impedance device further comprises:

providing current to a Reedswitch such that the Reedswitch acts as an open circuit in parallel with an inductor transreceiver coil.

24. The method of claim 15, wherein deactivating the low impedance device further comprises:

altering a signal provided to the low impedance device such that the low impedance device acts as an open circuit.

25. The method of claim 15, further comprising:

activating the low impedance device in response to an absence of detection of a proximally located programmer.

26. An implantable medical device capable of interacting with at least one implantable lead positioned within a heart of a patient, the implantable medical device also capable of communicating with a programmer located in proximity to the implantable medical device, the implantable medical device comprising:

a power source;

a programmer detector for detecting a presence of the programmer in proximity to the implantable medical device;

a communication system for communicating with the programmer;

an inductive transreceiver coil electrically coupled to the communication system for facilitating communication with the programmer; and a switch electrically coupled to the programmer detector and to the communication system in parallel with the inductive transreceiver coil, the switch opened in the presence of the programmer, thereby creating a communication path between the programmer and the communication system of the implantable medical device via the inductive transreceiver coil.

27. The implantable medical device of claim 26, wherein the programmer detector further comprises:

a detection switch which closes when the programmer detector detects the presence of the programmer in proximity to the implantable medical device, thereby providing a signal to the switch electrically coupled in parallel with the inductive transreceiver coil which causes the switch to open, thereby producing an open circuit.

28. The implantable medical device of claim 26, wherein the programmer detector further comprises:

a Hall sensor which senses a direct current magnetic filed radiating from the programmer when the programmer is located in proximity to the implantable medical device.

29. The method of claim 26, wherein the programmer detector further comprises:

a Reedswitch which closes when the programmer detector senses a direct current magnetic field radiating from the programmer indicating that the programmer is located in proximity to the implantable medical device.

30. The implantable medical device of claim 26, wherein the communications system further comprises:

a transreceiver capable of transmitting information between the implantable medical device and the programmer via the inductive transreceiver coil.

31. The implantable medical device of claim 26, wherein the inductive transreceiver coil facilitates transmission of inductive signals between the implantable medical device and the programmer.

32. The implantable medical device of claim 26, wherein the inductive transreceiver coil facilitates transmission of magnetically coupled signals between the implantable medical device and the programmer.

33. The implantable medical device of claim 26, wherein the inductive transreceiver coil receives data signals from the programmer.

34. The implantable medical device of claim 26, wherein the inductive transreceiver coil further comprises:

an aircoil.

35. The implantable medical device of claim 26, wherein the inductive transreceiver coil further comprises:

a ferrite coil.

36. The implantable medical device of claim 26, wherein the switch electrically coupled to the programmer detector and to the communication system further comprises:

a metal oxide semiconductor device.

37. The implantable medical device of claim 26, wherein the switch electrically coupled to the programmer detector and to the communication system further comprises:

a bipolar junction transistor.

38. The implantable medical device of claim 26, wherein the switch electrically coupled to the programmer detector and to the communication system further comprises:

a thyristor.

39. The implantable medical device of claim 26, wherein the switch electrically coupled to the programmer detector and to the communication system further comprises:

a triac.

40. The implantable medical device of claim 26, wherein the switch electrically coupled to the programmer detector and to the communication system further comprises:

a Reedswitch.

41. The implantable medical device of claim 26, wherein the switch electrically coupled to the programmer detector and to the communication system further comprises:

a junction field effect transistor.

42. An implantable medical device capable of interacting with at least one implantable lead positioned within a heart of a patient, the implantable medical device also capable of communicating with a programmer located in proximity to the implantable medical device, the implantable medical device comprising:

a power source;

programmer detector means for detecting a presence of the programmer in proximity to the implantable medical device;

communication means for communicating with the programmer;

inductive transreceiver coil means electrically coupled to the communication means for facilitating communication between the implantable medical device and the programmer; and switching means electrically coupled to the. programmer detector means and to the communication means, the switching means electrically coupled in parallel with the inductive transreceiver coil means such that the switching means is opened in the presence of the programmer, thereby creating a communication path between the programmer and the communication means of the implantable medical device via the inductive transreceiver coil means.

43. The implantable medical device of claim 42, wherein the programmer detector means further comprises:

detection switch means which closes when the programmer detector means detects the presence of a programmer in proximity to the implantable medical device, thereby providing a signal to the switching means electrically coupled in parallel with the inductive transreceiver coil means which causes the switching means to open, producing an open circuit.

44. The implantable medical device of claim 42, wherein the communication means further comprises:

transreceiver means capable of transmitting information between the implantable medical device and the programmer via the inductive transreceiver coil means.

45. The implantable medical device of claim 42, wherein the inductive transreceiver coil means facilitates transmission of inductive signals between the implantable medical device and the programmer.

46. The implantable medical device of claim 42, wherein the inductive transreceiver coil means facilitates transmission of magnetically coupled signals between the implantable medical device and the programmer.

47. The implantable medical device of claim 42, wherein the inductive transreceiver coil means receives data signals from the programmer.

48. An implantable medical device capable of interacting with at least one implantable lead position within a heart of a patient, the implantable medical device also capable of communicating with a programmer located in proximity to the implantable medical device, the implantable medical device comprising:

a printed circuit board interconnecting several components including:

a programmer detector for detecting a presence of the programmer in proximity to the implantable medical device;

a communication system for communicating with the programmer;

a switch electrically coupled to the programmer detector and to the communication system, the switch opened in the presence of the programmer;

a control coupled to the switch for opening the switch;

a power source electrically coupled to the printed circuit board; and an inductive transreceiver coil electrically coupled to the printed circuit board in parallel with the switch.

49. The implantable medical device of claim 48, and further comprising:

a frame surrounding the printed circuit board and the power source, wherein the inductive transreceiver coil resides within the frame.

50. The implantable medical device of claim 48, wherein the inductive transreceiver coil further comprises:

an aircoil.

51. The implantable medical device of claim 48, wherein the programmer detector further comprises:

a Reedswitch.

52. The implantable medical device of claim 48, wherein the programmer detector further comprises:

a Hall switch.

53. The implantable medical device of claim 48, wherein the switch further comprises:

a metal oxide semiconductor device.

54. The implantable medical device of claim 48, wherein the switch further comprises:

a Reedswitch.

55. The implantable medical device of claim 48, wherein the switch further comprises:

a bipolar junction transistor.

56. The implantable medical device of claim 48, wherein the switch further comprises:

a thyristor.

57. The implantable medical device of claim 48, wherein the switch further comprises:

a triac.

58. The implantable medical device of claim 48, wherein the switch further comprises:

a junction field effect transistor.

* * * * *

UNITED STATES PATENT AND TRADEMARK OFFICE
CERTIFICATE OF CORRECTION

| | | |
|---|---|---|
| PATENT NO. | : 6,510,345 B1 | Page 1 of 1 |
| APPLICATION NO. | : 09/556454 | |
| DATED | : January 21, 2003 | |
| INVENTOR(S) | : Maarten M. P. E. Van Bentem | |

It is certified that error appears in the above-identified patent and that said Letters Patent is hereby corrected as shown below:

Column 20,
Line 45, delete "at least on e" and insert -- at least one --.

Column 23,
Line 16, delete "to the. programmer" and insert -- to the programmer --.

Signed and Sealed this

Twenty-seventh Day of June, 2006

JON W. DUDAS
*Director of the United States Patent and Trademark Office*